(12) United States Patent
Sode

(10) Patent No.: US 7,497,940 B2
(45) Date of Patent: Mar. 3, 2009

(54) GLUCOSE SENSOR AND GLUCOSE LEVEL MEASURING APPARATUS

(76) Inventor: Koji Sode, 1-13-16, Minami Meguro-ku, Tokyo (JP) 152-0013

( * ) Notice: Subject to any disclaimer, the term of this patent is extended or adjusted under 35 U.S.C. 154(b) by 361 days.

(21) Appl. No.: 10/568,348

(22) PCT Filed: Sep. 1, 2004

(86) PCT No.: PCT/JP2004/012625

§ 371 (c)(1),
(2), (4) Date: Feb. 21, 2006

(87) PCT Pub. No.: WO2005/023111

PCT Pub. Date: Mar. 17, 2005

(65) Prior Publication Data

US 2006/0258959 A1 Nov. 16, 2006

(30) Foreign Application Priority Data

Sep. 2, 2003 (JP) .............................. 2003-310019

(51) Int. Cl.
*C12Q 1/00* (2006.01)
(52) U.S. Cl. .................................................. 205/777.5
(58) Field of Classification Search .............. 205/777.5; 204/403.04; 435/14, 26
See application file for complete search history.

(56) References Cited

U.S. PATENT DOCUMENTS 5,372,133 A * 12/1994 Hogen Esch ................ 600/377

| 7,094,585 B2 * | 8/2006 | Sode | 435/190 |
| 7,244,600 B2 * | 7/2007 | Sode et al. | 435/190 |
| 2005/0067278 A1 | 3/2005 | Sode | |
| 2006/0035300 A1 * | 2/2006 | Yamaoka et al. | 435/14 |
| 2006/0094098 A1 * | 5/2006 | Yamaoka et al. | 435/189 |
| 2006/0211094 A1 * | 9/2006 | Sode | 435/69.1 |
| 2006/0252123 A1 * | 11/2006 | Sode | 435/69.1 |

FOREIGN PATENT DOCUMENTS

| JP | 6-7324 | 1/1994 |
| JP | 08-010208 | 1/1996 |
| JP | 9-503924 | 4/1997 |
| WO | WO 95/02357 | 1/1995 |
| WO | WO 02/073181 | 9/2002 |

OTHER PUBLICATIONS

Inose, K. et al. Cloning and Expression of the Gene Encoding Catalytic Subunit of Thermostable GDH from Burkholderia cepacia in *E. coli*. Biochimica et Biophysica Acta 1645(2)133-138, Feb. 21, 2003.*

* cited by examiner

*Primary Examiner*—Ralph Gitomer
(74) *Attorney, Agent, or Firm*—Hamre, Schumann, Mueller & Larson, P.C.

(57) ABSTRACT

The present invention relates to a glucose sensor (2) including an electrode (32) which includes a conductive component and glucose dehydrogenase immobilized to the conductive component. As the glucose dehydrogenase, use is made of a protein complex including a catalytic activity subunit which has glucose dehydrogenase activity, and an electron mediator subunit for supplying an electron donated from the catalytic activity subunit to the conductive component. Preferably, the glucose sensor (2) is designed to continuously measure the glucose level or successively measure the glucose level a plurality of times.

17 Claims, 8 Drawing Sheets

GLUCOSE SENSOR AND GLUCOSE LEVEL MEASURING APPARATUS

TECHNICAL FIELD

The present invention relates to a technique to measure the glucose level in a sample.

BACKGROUND ART

For diabetics, it is important to know their own glucose levels and it is necessary to decide the timing of insulin administration by repetitively measuring the glucose levels. For example, the glucose level measurement is performed using a disposable glucose sensor (See Patent Document 1: JP-B-H08-10208, for example). To measure the glucose level using the glucose sensor disclosed in the document, blood need be extracted from the skin using a lancing apparatus. Therefore, the monitoring of the glucose level is troublesome for diabetics, and the necessity of sticking a needle into the skin at each time of glucose level measurement causes pain.

To solve such problems, a technique to continuously monitor the glucose level has been proposed (See Patent Document 2: JP-A-H09-503924, for example), which has been commercialized as "Gluco Watch" in the United States. The glucose level measuring technique employs an electrode method in which blood or interstitial fluid extracted from the skin is supplied to an electrode to measure the glucose level by using the electrode. The electrode in this case is arranged in close proximity to the skin in measuring the glucose level and is designed so that an electron taken from the blood or interstitial fluid via glucose oxidase (hereinafter, sometimes simply referred to as "GOD" is supplied to the electrode (conductive component).

The electrode method using GOD has a drawback that the accuracy of measurement may be deteriorated by the influence of dissolved oxygen in the sample (blood or interstitial fluid). Generally, in the method using GOD, the supply of the electron, which GOD took from glucose, to the electrode (conductive component) is performed by either of the following two methods: in one of the methods, hydrogen peroxide is generated so that the electron is supplied to the electrode (conductive component) via hydrogen peroxide, whereas, in the other method, the electron is supplied to the electrode (conductive component) via an electron mediator (e.g. metal complex such as potassium ferricyanide). Both of the methods hardly cause problems to the human body as long as the measurement of the glucose level using blood or the like extracted from the skin is performed at a place separated from the skin. However, considering that hydrogen peroxide and potassium ferricyanide are the substances which are not good for the human body, the method in which the electrode containing GOD is disposed in close proximity to the skin, like the forgoing method, is not preferable.

Further, in the method which utilizes an electron mediator, it is necessary to add an electron mediator into the electrode or mobilize an electron mediator at the electrode surface. In both cases, the preparation of an electron mediator separately from GOD and adding the electron mediator to the electrode is disadvantageous in terms of cost.

Patent Document 1: JP-B-H08-10208
Patent Document 2: JP-A-H09-503924

DISCLOSURE OF THE INVENTION

An object of the present invention is to make it possible to measure a glucose level without causing adverse effect on the human body and advantageously in terms of cost.

According to a first aspect of the present invention, there is provided a glucose sensor comprising an electrode including a conductive component and glucose dehydrogenase immobilized to the conductive component. The glucose dehydrogenase is a protein complex including a catalytic activity subunit in which flavin adenine dinucleotide is bound as coenzyme and which has glucose dehydrogenase activity, and an electron mediator subunit for supplying an electron donated from the catalytic activity subunit to the conductive component.

According to a second aspect of the present invention, there is provided a glucose level measuring apparatus designed to continuously measure a glucose level or successively measure a glucose level a plurality of times based on blood or interstitial fluid sampled from subcutaneous tissue. The apparatus comprises a glucose sensor including an electrode which includes a conductive component and glucose dehydrogenase immobilized to the conductive component, a measurer for measuring response quantity related to the amount of electron transfer between the blood or interstitial fluid and the electrode, a computation unit for computing a glucose level based on the measurement by the measurer, and a controller for controlling the timing at which the glucose level is computed at the computation unit. The glucose dehydrogenase is a protein complex including a catalytic activity subunit in which flavin adenine dinucleotide is bound as coenzyme and which has glucose dehydrogenase activity, and an electron mediator subunit for supplying an electron donated from the catalytic activity subunit to the conductive component.

As the glucose dehydrogenase, it is preferable to use one that derives from a microorganism belonging to the genus *Burkholderia*.

Herein, the microorganism belonging to the genus *Burkholderia* is not limitative as long as it can produce an enzyme including an α subunit (catalytic activity subunit) having glucose dehydrogenase activity or cytochrome c (β subunit) (hereinafter, sometimes simply referred to as "GDH") However, among such microorganisms, it is preferable to use *Burkholderia cepacia*, and particularly to use *Burkholderia cepacia* KS1 strain (hereinafter, sometimes simply referred to as "KS1 strain").

The KS1 strain is a novel strain separated from the soil near hot springs and identified as *Burkholderia cepacia* based on the mycological characteristics. The KS1 strain was deposited to International Patent Organism Depositary of National Institute of Advanced Industrial Science and Technology (Tsukuba Central 6, 1-1-1 Higashi, Tsukuba, Ibaraki 305-8566 Japan) as the microorganism deposit No. FERM BP-7306 on Sep. 25, 2000. The KS1 strain, details of which are disclosed in WO 02/36779, can produce GDH which includes an α subunit (molecular weight: about 60 kDa) which is a catalytic activity subunit, a β subunit (molecular weight: about 43 kDa) corresponding to cytochrome c which is an electron mediator subunit, and a γ subunit (molecular weight: about 14 kDa). It is to be noted that the above molecular weights are measured in SDS-polyacrylamide gel electrophoresis under reduction conditions.

Although the α subunit, cytochrome c (the β subunit) or the γ subunit is specified in the claims of the present application, it is just for expediency to specify each subunit. Therefore, the use of GDH, which is obtained from a transformant provided by transferring the vector including the expression code of the intended subunit to the host for transformation, as glucose dehydrogenase is included in the technical scope of the present invention when the only difference is the origin of the GDH (subunit).

For instance, the glucose sensor is designed to continuously measure the glucose level or successively measure the glucose level a plurality of times. In this case, the glucose sensor further comprises a sampler for sampling blood or interstitial fluid from subcutaneous tissue, and the blood or interstitial fluid sampled by the sampler is brought into contact with the electrode.

The sampler comprises a hollow lancing needle for lancing skin and a liquid reservoir for reserving the blood or interstitial fluid sampled through the lancing needle. In this case, the blood or interstitial fluid reserved in the liquid reservoir is brought into contact with the electrode.

For instance, the liquid reservoir comprises a porous body arranged in contact with the electrode and the lancing needle.

The glucose sensor may be used with at least part of the electrode embedded in subcutaneous tissue. In this case, the electrode is provided on a flexible insulating substrate.

BEST MODE FOR CARRYING OUT THE INVENTION

Figure 1:
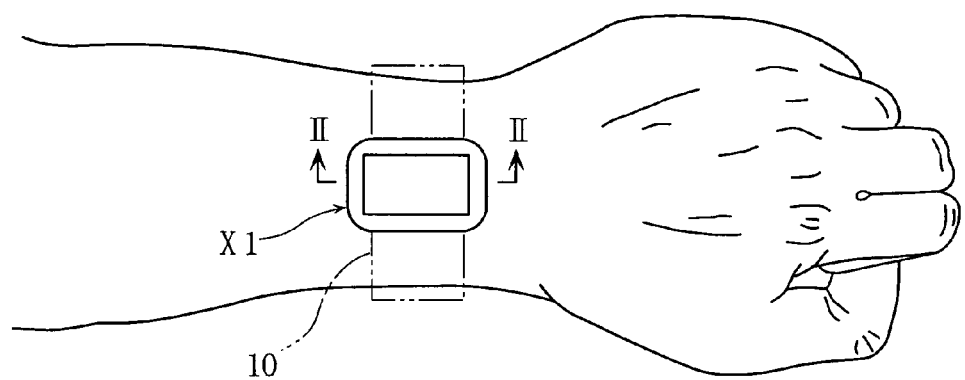
FIG. 1 is a front view showing a glucose level measuring apparatus according to a first embodiment of the present invention.
Figure 2:
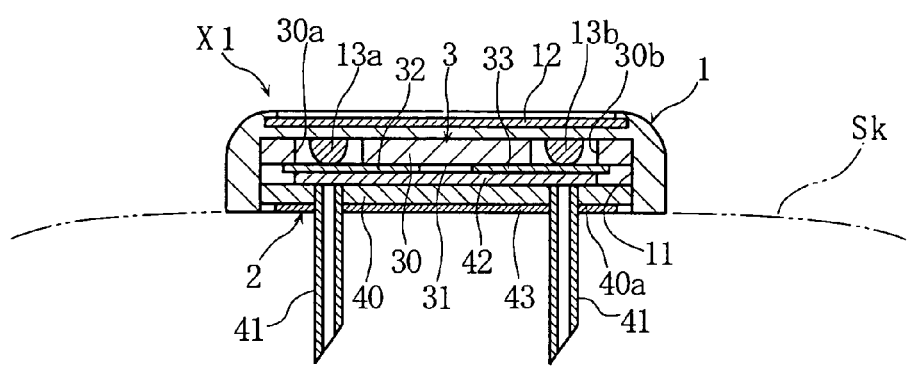
FIG. 2 is a sectional view taken along lines II-II in FIG. 1.
Figure 3:
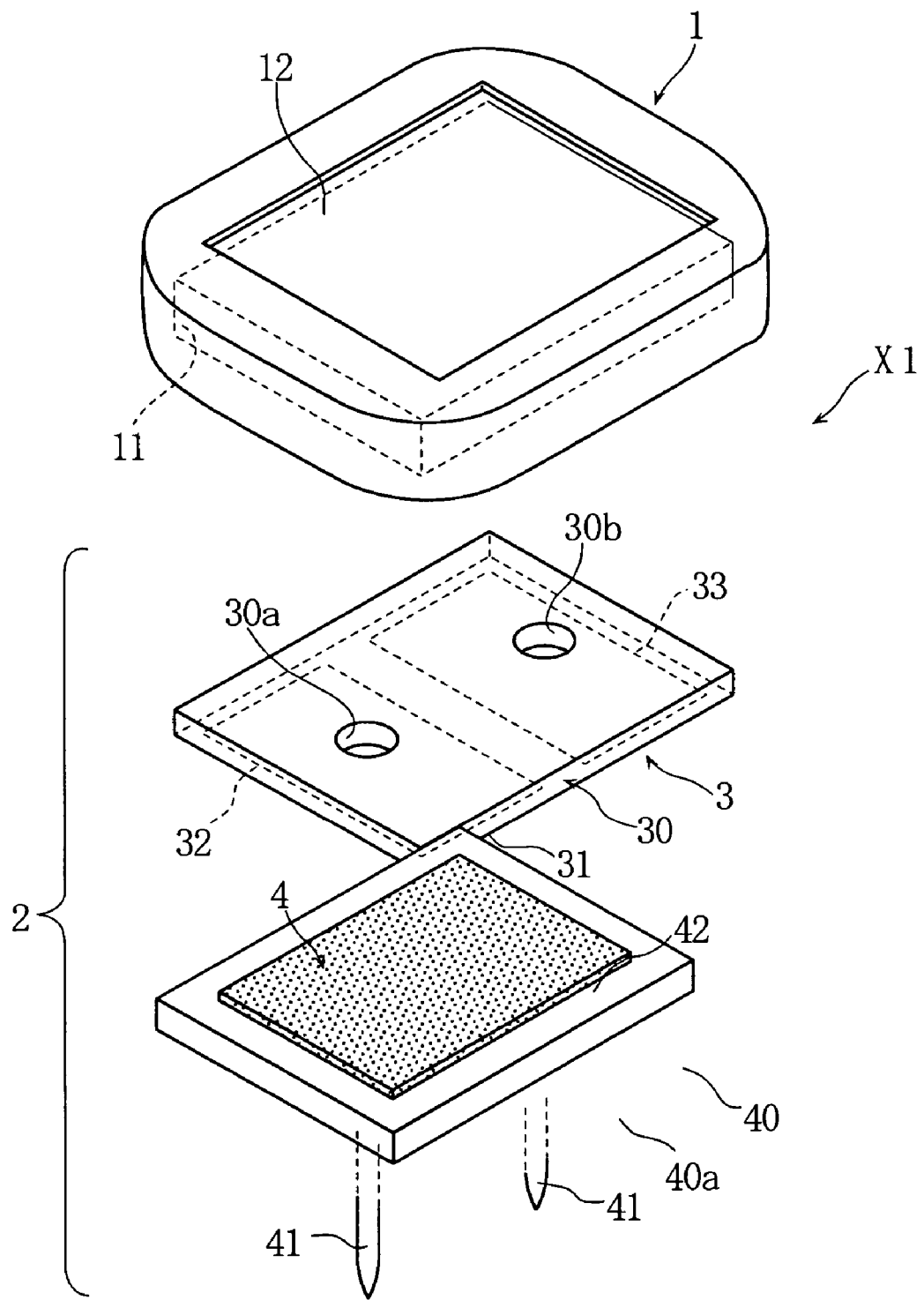
FIG. 3 is an exploded perspective view of the glucose measuring apparatus shown in FIGS. 1 and 2.

The glucose level measuring apparatus X1 shown in FIG. 1 is designed to be used in close contact with the skin of an arm, for example, and to continuously measure the glucose level or successively measure the glucose level a plurality of times. As shown in FIGS. 2 and 3, the glucose level measuring apparatus X1 includes a housing 1 and a glucose sensor 2.

The housing 1 is, in use, fixed to e.g. an arm by using a band 10 (See FIG. 1) and includes a recess 11, a display 12, a pair of connector pins 13a, 13b and a non-illustrated control circuit. The recess 11 serves to removably accommodate the glucose sensor 2. The display 12 mainly displays the measurement results and comprises an LCD, for example. The connector pins 13a and 13b are portions to come into contact with the working electrode 32 or the counter electrode 33 of the glucose sensor 2, which will be described later. The connector pins 13a and 13b are used for applying a voltage between the working electrode 32 and the counter electrode 33 of the glucose sensor 2 and for measuring the response current when the voltage is applied.

The glucose sensor 2 includes a sensor body 3 and a sampler 4 which are bonded together and removably mounted, as one piece, to the housing 1. The glucose sensor 2 may be disposable, for example. Alternatively, the sensor body 3 and the sampler 4 may be mounted to the housing 1 to be removable individually so that the sensor body 3 and the sampler 4 can be exchanged individually.

The sensor body 3 includes an insulating substrate 30 having a lower surface 31 on which the working electrode 32 and the counter electrode 33 are provided. The insulating substrate 30 is formed with a pair of through-holes 30a and 30b. The through-hole 30a exposes the working electrode 32, whereas the through-hole 30b exposes the counter electrode 33. With such a structure of the sensor body 3, when the glucose sensor 2 is mounted in the recess 11 of the housing 1, the connector pin 13a comes into contact with the working electrode 32, whereas the connector pin 13b comes into contact with the counter electrode 33.

The working electrode 32 includes a conductive component and glucose dehydrogenase (GDH) and is fixed to the insulating substrate 30 using a crosslinking agent such as glutaraldehyde.

For instance, the conductive component comprises carbon powder, and the content is 5 to 100 mg. Alternatively, as the conductive component, use may be made of conductive powder other than carbon powder or a conductor made into a porous state (e.g. sintered body of conductive powder).

As the GDH, use is made of a protein complex comprising a catalytic activity subunit having glucose dehydrogenase activity and an electron mediator subunit which are bound to each other.

The catalytic activity subunit serves to take an electron from glucose in a sample and supply the electron to the electron mediator subunit. As the catalytic activity subunit, one that includes flavin adenine dinucleotide (FAD) as coenzyme is used. Thus, to the electron mediator subunit, the electron from the catalytic activity subunit is supplied via reduced FAD.

The content of catalytic activity corresponds to 5 to 100 U when converted into activity, for example. Herein, enzyme one unit (1 U) is defined as the quantity which oxidizes 1 μM of glucose per one minute when fading with time due to reduction of DCIP (2,6-dichlorophenol-indophenol) is measured at 600 nm, which is the absorption wavelength of DCIP, under standard test conditions (pH 6.0, 37° C.) (the molar extinction coefficient is 4.76×1000 μM/cm).

The electron mediator subunit serves to supply the electron received from the catalytic activity subunit to the conductive component. As the electron mediator subunit, use is made of cytochrome c, for example.

As the catalytic activity subunit and the electron mediator subunit, it is preferable to use a microorganism belonging to the genus *Burkholderia*, such as a protein complex originating from a KS1 strain. The GDH originating from a KS1 strain is produced as a trimer comprising an α subunit serving as a catalytic activity subunit (the molecular weight in the SDS-polyacrylamide gel electrophoresis under the reduction conditions is about 60 kDa), a β subunit which is electron mediator protein (the molecular weight in the SDS-polyacrylamide gel electrophoresis under the reduction conditions is about 43 kDa), and a γ subunit (the molecular weight in the SDS-polyacrylamide gel electrophoresis under the reduction conditions is about 14 kDa), or as a dimer comprising the α subunit and the β subunit. Alternatively, as GDH, use may be made of a protein complex produced by a transformant in which DNA that codes for the α subunit, the β subunit and the γ subunit is transferred.

The obtaining of intended GDH from the above-described microorganism or transformant is advantageous in terms of cost, because it eliminates the need for individually purifying or preparing the subunits (protein) and adding the electron mediator into the working electrode 32 separately from GDH.

The counter electrode 33 may be formed by screen-printing carbon paste, for example. The counter electrode 33 may be made of a conductive component other than carbon and by a technique other than screen printing.

The sampler 4 is used to exiract a sample (blood or interstitial fluid) from the skin and includes an insulating substrate 40, a lancing needle 41 and a liquid absorber 42 as a liquid reservoir.

The insulating substrate 40 serves to fix the lancing needle 41 and the liquid absorber 42 and has a lower surface 40a to which an adhesive tape 43 having opposite adhesive surfaces is bonded. As a result, the insulating substrate 40 and hence the glucose sensor 2 can be fixed to the skin Sk in close contact therewith. The lancing needle 41 serves to lance the skin to extract sample and has a hollow structure. The lancing needle 41 penetrates through the insulating substrate 40 and is open at the upper surface of the insulating substrate 40. The liquid absorber 42 serves to retain the sample extracted by the lancing needle 41 and is arranged to cover the upper end of the lancing needle 41. When the glucose sensor 2 is accommodated in the housing 1, the liquid absorber 42 comes into contact with the working electrode 32 and the counter electrode 33. For instance, the liquid absorber 42 comprises a porous body. As the porous body, use may be made of woven fabric, nonwoven fabric, knitted fabric or a expanded body. Instead of providing the liquid absorber 42, a space for retaining the extracted sample may be provided.

Figure 4:
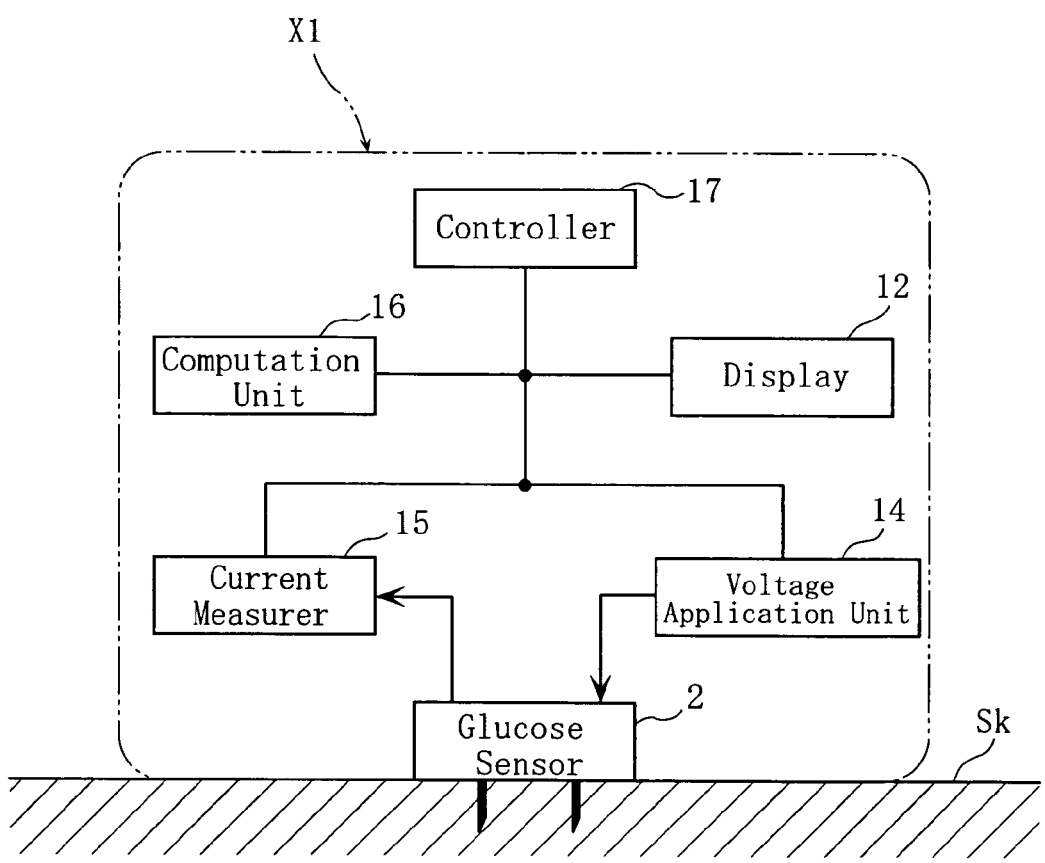
FIG. 4 is a block diagram of the glucose level measuring apparatus shown in FIGS. 1 and 2.

As shown in FIG. 4, in addition to the elements described above, the glucose level measuring apparatus X1 includes a voltage application unit 14, a current measurer 15, a computation unit 16 and a controller 17.

The voltage application unit 14 serves to apply a voltage to the working electrode 32 and the counter electrode 33 and is electrically connected to the connector pins 13a and 13b (See FIG. 2), though not illustrated.

The current measurer 15 serves to measure the response current when voltage is applied between the working electrode 32 and the counter electrode 33.

The computation unit 16 serves to compute the glucose level in the sample based on the response current measured at the current measurer 15.

The controller 17 controls the operation of each unit 12, 14-16. Specifically, the controller controls the current measurer 15 to control the timing at which the response current is measured, controls the computation unit 16 to make the unit perform the computation of the glucose level, or controls the display 12 to control the content of display at the display 12.

As better shown in FIG. 2, by fixing the glucose sensor 2 to the skin Sk and then covering the glucose sensor 2 with the housing 1, the glucose level measuring apparatus X1 can continuously measure the glucose level or successively measure the glucose level a plurality of times. When the glucose sensor 2 is fixed to the skin Sk, the lancing needle 41 of the sampler 4 sticks into the skin Sk. Since the lancing needle 41 is hollow, sample is introduced to the liquid absorber 42 through the lancing needle 41. In this state, liquid junction is made between the liquid absorber 42 and the subcutaneous tissue. Therefore, when the glucose level in the subcutaneous tissue changes, the glucose level in the liquid absorber 42 changes to equilibrate with the glucose level in the subcutaneous tissue. In this way, the glucose level in the liquid absorber 42 reflects the glucose level in the subcutaneous tissue.

The liquid absorber 42 is held in contact with the working electrode 32. Therefore, the catalytic activity subunit in the working electrode 32 takes an electron from glucose in the sample. The electron is supplied to the electron mediator subunit. A potential difference is continuously applied between the working electrode 32 and the counter electrode 33 by the voltage application unit 14 shown in FIG. 4 to prevent the accumulation of electrons in the electron mediator subunit more than necessary and to measure the response current in real time. Due to the potential difference applied between the working electrode 32 and the counter electrode 33, the electron donated to the electron mediator subunit is supplied to the conductive component. Since the working electrode 32 is connected to the current measurer 15 via the connector pin 13a, the current measurer 15 measures the amount of electrons supplied from the electron mediator subunit as the response current.

The controller 17 shown in FIG. 4 samples the response current continuously or with a predetermined time interval (every five minutes or every two hours or inbetween, for example) and makes the computation unit 16 compute the glucose level continuously or with a predetermined time interval based on the sampled response current. The computation unit 16 computes the glucose level by applying the measured response current to the calibration curve obtained in advance. When the computation of the glucose level is completed, the controller 17 makes the display 12 display the result of the glucose level computation performed by the computation unit 16.

In the working electrode 32 of the glucose sensor 2, GDH is contained as the enzyme in which the electron mediator subunit is bound to the catalytic activity subunit. Therefore, in the working electrode 32, the protein having a function to transfer electrons to the working electrode 32 (electron mediator subunit) exists uniformly around the protein which has catalytic activity (catalytic activity subunit). Specifically, with respect to the protein having catalytic activity (catalytic activity subunit), the electron mediator protein (electron mediator subunit) of the amount equal to the catalytic activity subunit in the number of molecules exists in close contact with the catalytic activity subunit. As a result, in the glucose sensor 2, the rate of reaction (electron transfer) between the catalytic protein and the electron mediator protein is increased, which leads to the improvement of the response sensitivity and enables stable measurement of the response current.

Figure 5:
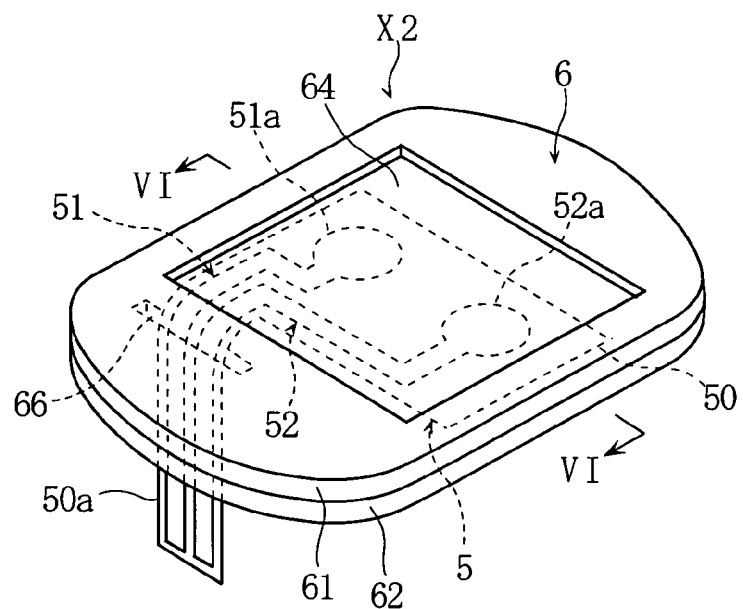
FIG. 5 is a perspective view showing a glucose level measuring apparatus according to a second embodiment of the present invention.
Figure 6:
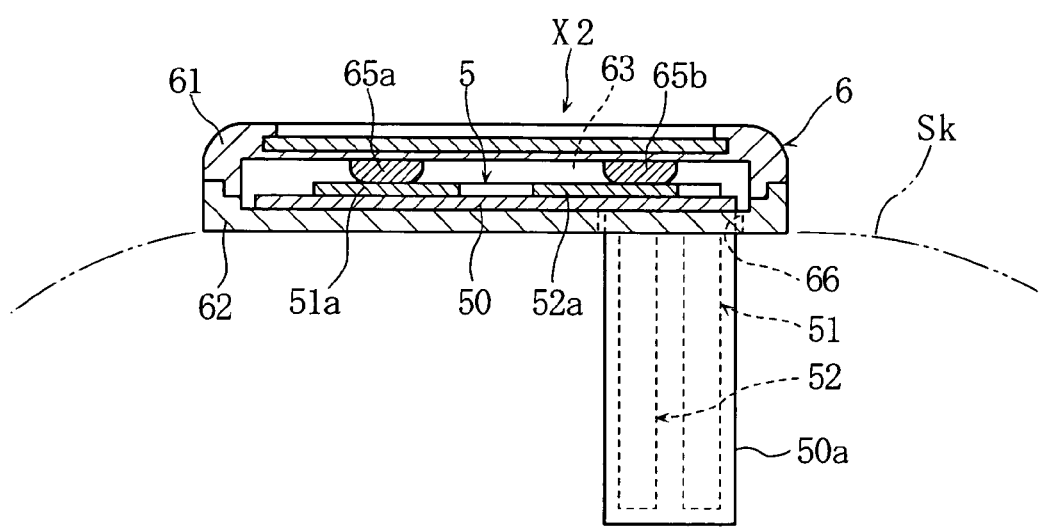
FIG. 6 is a sectional view taken along lines VI-VI in FIG. 5.

With reference to FIGS. 5 and 6, a second embodiment of the present invention will be described. Similarly to the glucose level measuring apparatus X1 of the first embodiment, the glucose level measuring apparatus X2 shown in FIGS. 5 and 6 is designed to be used in close contact with the skin Sk of an arm, for example, by utilizing a band or an adhesive tape (See FIG. 1). The glucose level measuring apparatus X2 is designed to continuously measure the glucose level or successively measure the glucose level a plurality of times and includes a glucose sensor 5 and a housing 6.

The glucose sensor 5 is removably attachable to the housing 6 and may be disposable, for example. The glucose sensor 5 includes an insulating substrate 50 on which an working electrode 51 and a counter electrode 52 are formed. The insulating substrate 50 includes a narrow portion 50a for sticking into the skin Sk and is made of e.g. polyimide resin to be flexible. The working electrode 51 and the counter electrode 52 include respective terminals 51a and 52a. The working electrode 51 and the counter electrode 52 are formed similarly to the working electrode 32 and the counter electrode 33 (See FIG. 3) of the foregoing glucose sensor 2.

The housing 6 includes a first and a second members 61 and 62 between which a space 63 is defined. The space 63 is used for accommodating the glucose sensor 5.

The first member 51 is provided with a display 64 and a pair of connector pins 65a and 65b. The display 64 serves to display various information and may comprise an LCD, for example. The connector pins 65a and 65b are connected to a non-illustrated control circuit, and come into contact with the terminals 51a and 52a of the working electrode 51 and the counter electrode 52 when the glucose sensor 5 is retained in the space 63. In this state, voltage can be applied between the working electrode 51 and the counter electrode 52 by utilizing the connector pins 65a and 65b, and the current in applying the voltage can be measured. The second member 62 is formed with an opening 66 for allowing the narrow portion 50a of the insulating substrate 50 to project out.

With the glucose level measuring apparatus X2, by mounting the glucose sensor 5 to the housing 6 and sticking the narrow portion 50a of the insulating substrate 50 into the skin Sk, continuous measurement of the glucose level or successive measurement of the glucose level a plurality of times can be performed.

In the state in which the narrow portion 50a of the insulating substrate 50 is stuck into the skin Sk, an electron is taken out from glucose in blood or interstitial fluid at the working electrode 51. The electron is supplied to the electron mediator subunit. The electron donated to the electron mediator subunit is supplied to the conductive component of the working electrode 51 by applying a potential difference between the working electrode 51 and the counter electrode 52. The amount of electrons donated in this way is measured as the response current via the connector pins 65a and 65b. In the glucose level measuring apparatus X2, the response current is sampled continuously or with a predetermined time interval (every five minutes or every two hours or in between, for example), and the glucose level is computed continuously or with a predetermined time interval based on the sampled response current. The computation results are displayed at the display 64.

In the glucose sensor 5 again, the working electrode 51 includes a protein complex in which the catalytic activity subunit and the electron mediator subunit are bound together.

Therefore, the glucose sensor 5 does not have an adverse effect on the human body, and stable measurement of the response current can be performed advantageously in terms of cost.

EXAMPLE 1

In this example, the response characteristics of enzyme electrodes were examined using a batch reaction vessel.

The enzyme electrodes had a structure in which an enzyme and carbon powder were immobilized within a plastic tube (diameter 5 mm, length 30 mm). The immobilization of the enzyme and the carbon powder was performed by loading a mixture of the enzyme and the carbon paste (20 mg) into a plastic tube and then impregnating 100 mM of sodium phosphate buffer solution (pH 7.0) including 1% of glutaraldehyde as a cross-linking agent into the plastic tube. An excess of aldehyde groups in the cross-linking agent was inactivated by treating in 10 mM of Tris-HCl for 20 minutes. The enzyme electrode was equilibrated, before use, by immersing in 100 mM of sodium phosphate buffer solution (pH 7.0). As the enzyme, use was made of CyGDH (92.1 U/mg) comprising an α subunit (catalytic activity subunit) originating from the KS1 strain, a β subunit (electron mediator subunit) and a γ subunit, or αGDH (21.3 U/mg) comprising an α subunit (catalytic activity subunit) originating from the KS1 strain and a γ subunit, whereby two kinds of enzyme electrodes were prepared. In the enzyme electrodes, the content of the enzyme was set to the amount corresponding to 10 U.

The response characteristics were examined based on the response current measured with respect to glucose solutions of different concentrations. The response current was measured by immersing an enzyme electrode, a reference electrode and a counter electrode in a reaction vessel retaining the glucose solution adjusted to the intended concentration, applying a voltage between the enzyme electrode and the counter electrode and using the reference electrode as the base electrode. Glucose solutions were prepared by dissolving glucose in 100 mM of sodium phosphate buffer solution (pH 7.0). The concentrations of the glucose solutions were 0 mM, 0.5 mM, 1.0 mM, 1.5 mM, 2.0 mM, 2.5 mM, 8 mM, 12 mM, 21 mM, 30 mM and 47 mM, respectively. An Ag/AgCl electrode was used as the reference electrode, whereas a Pt electrode was used as the counter electrode. The applied voltage was +400 mV. The measurement of the response current was performed while maintaining the temperature of the reaction vessel at 25° C. or 37° C. The measurements of the response current are shown in FIG. 8.

Figure 8:
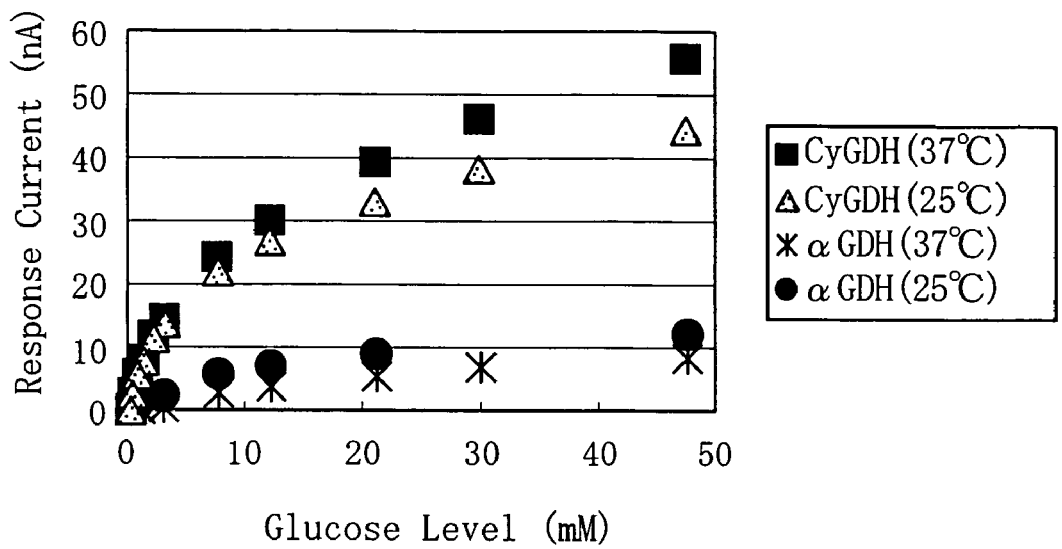
FIG. 8 is a graph showing the measurements of responsive current in the case where the glucose level was changed in Example 1.

As is clear from FIG. 8, in the case of the enzyme electrode using αGDH which does not include a β subunit, the increment of the response current in accordance with the increase of the glucose level is small, which indicates that proper electron transfer is not performed between the conductive component and the α subunit of the working electrode. On the other hand, in the case of the enzyme electrode using CyGDH including a β subunit, the increment of the response current in accordance with the increase of the glucose level is large, and good response characteristics are obtained. This indicates that, by combining the β subunit to the α subunit, proper electron transfer is performed between the conductive component and the α subunit of the working electrode. The above phenomenon is seen in both of the case where the temperature during the measurement is set to 25° C. and the case where the temperature during the measurement is set to 37° C. Therefore, with the enzyme electrode using GDH in which electron mediator protein is combined, the glucose level can be measured by the electrode method without using an electron mediator such as a metal complex.

EXAMPLE 2

In this example, the influence of the voltage application on the response characteristics of an enzyme electrode was examined using a batch reaction vessel. The enzyme electrode was prepared in a similar manner to Example 1. As the enzyme, however, CyGDH with a specific activity of 56.5 U/mg was used. The content of the enzyme in the enzyme electrode was set to the amount corresponding to 50 U. The response characteristics were examined based on the response current measured with respect to each of the cases where the voltage of +400 mV was applied and where the voltage of +250 mV was applied while maintaining the glucose solutions of the intended concentrations at 37° C. The concentrations of the glucose solutions were 0 mM, 0.5 mM, 1.0 mM, 1.5 mM, 2.0 mM, 2.5 mM, 8 mM, 12 mM, 21 mM and 47 mM, respectively. The measurements of the response current are shown in FIG. 9.

Figure 9:
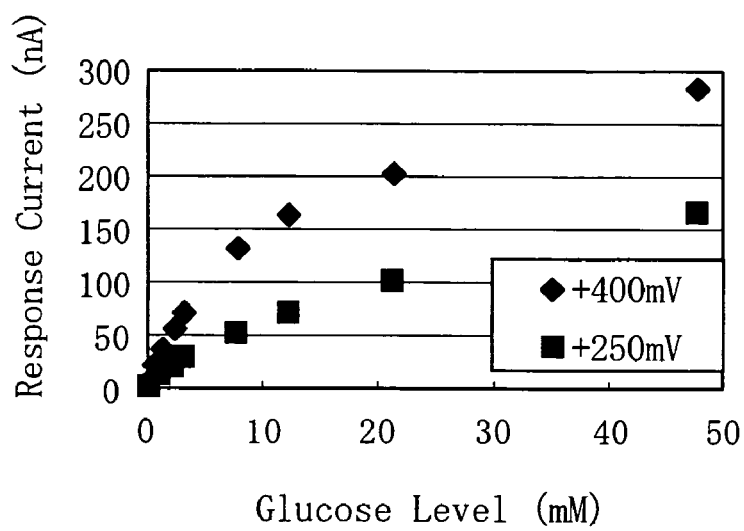
FIG. 9 is a graph showing the measurements of responsive current in the case where the glucose level was changed in Example 2.

As is clear from FIG. 9, although the response current in the case where the applied voltage is +250 mV is smaller than that in the case where the applied voltage is +400 mV, the response current is properly measured in both cases. In this way, when the GDH in which the electron mediator protein is combined is used, the response current and hence the glucose level can be properly measured even when the applied voltage is relatively small. This is advantageous in the case where continuous voltage application is necessary, such as when continuous or successive monitoring of the glucose level is performed, or in the case where the glucose level measuring apparatus for continuous or successive monitoring of the glucose level is driven by a battery.

EXAMPLE 3

In this example, the capability of continuous monitoring of the glucose level using an enzyme electrode was examined using a flow cell. Specifically, (1) 72-hour continuous monitoring test was performed, and (2) an enzyme electrode immediately after the production (unused) and an enzyme electrode after used for the 72-hour continuous monitoring were checked for the response characteristics.

(1) Continuous Monitoring Test

Figure 7:
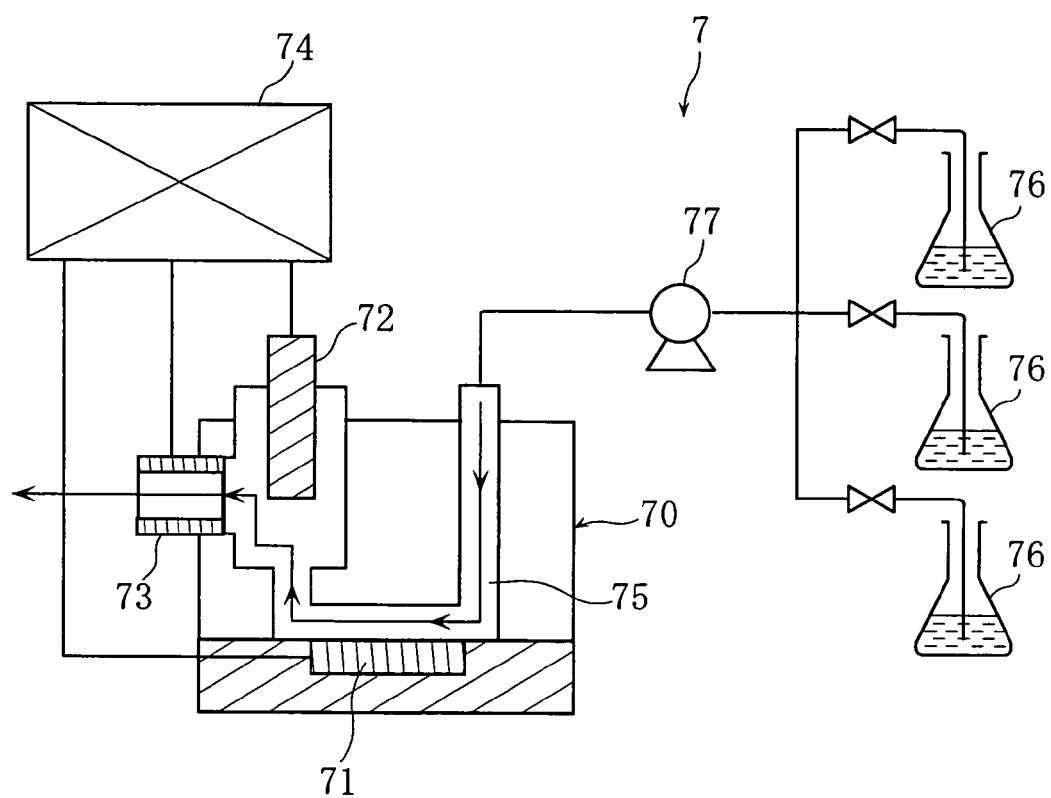
FIG. 7 is a schematic structural view of the measurement system used in Example 3.

The continuous monitoring test was performed using a measurement system 7 schematically shown in FIG. 7. The measurement system 7 includes a reaction cell 70 in which an enzyme electrode 71, a reference electrode 72 and a counter electrode 73 are retained so that the electrodes 71-73 come into contact with the glucose solution supplied into the reaction cell 70. Each of the electrodes 71-73 is connected to a potentiostat 74. A flow path 75 is defined in the reaction cell 70, and the reaction cell 70 is structured as a flow cell capable of continuously supplying/discharging the glucose solution. Specifically, the glucose solution of the intended concentration is retained in a container 76 and continuously supplied to the reaction cell 70 by the power of a pump 77. In the measurement system 7, an enzyme electrode prepared in the same manner as Example 2 was used as the enzyme electrode 71, an Ag/AgCl electrode for a flow cell was used as the reference electrode 72, and a stainless tube was used as the counter electrode 73.

Figure 10:
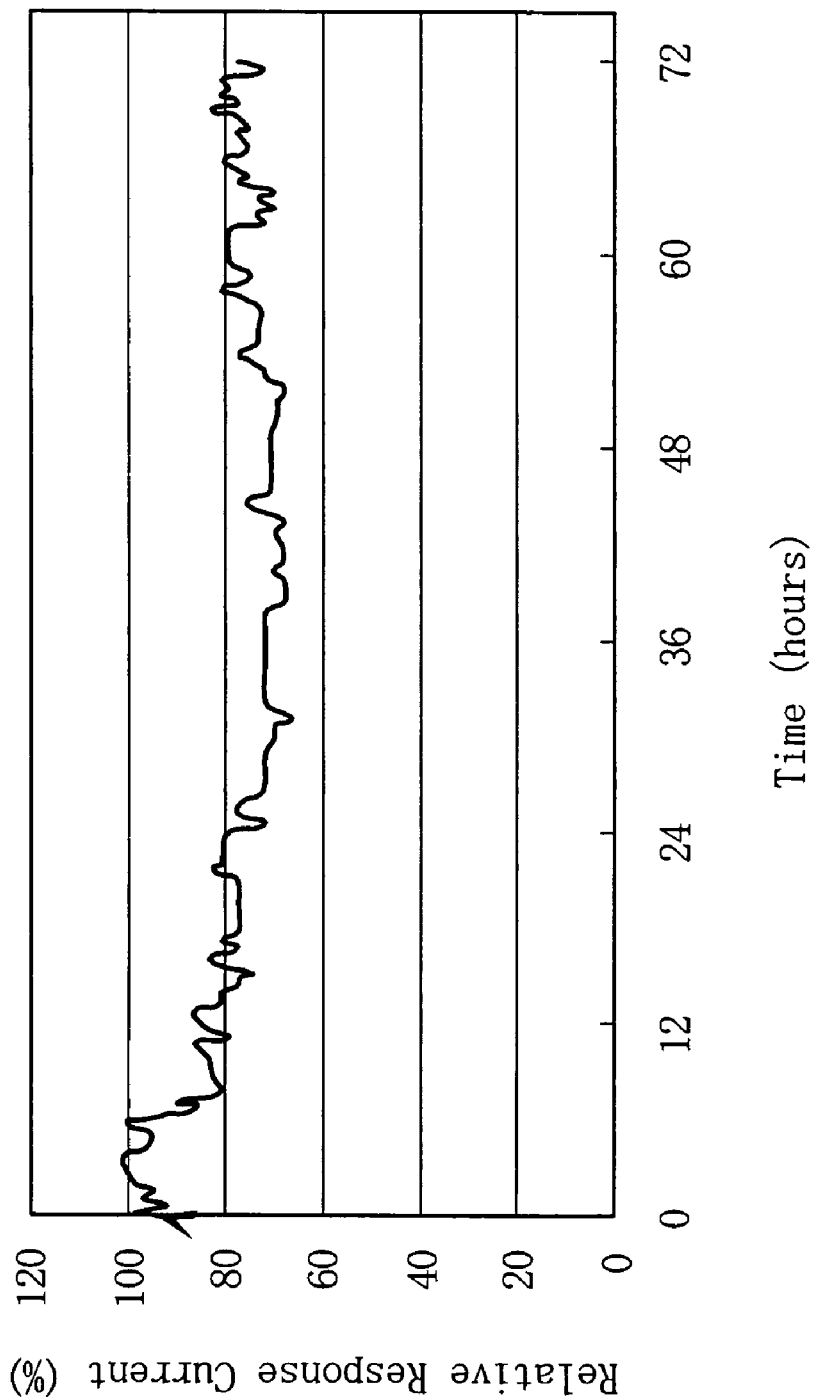
FIG. 10 is a graph showing the change of responsive current with time in the case where the glucose level was maintained constant in Example 3.

A voltage was applied between the enzyme electrode 71 and the counter electrode 73, and the response current was measured using the reference electrode 72 as the base electrode. The applied voltage was +250 mV. The response current was measured continuously while continuously supplying 5 mM of glucose solution (pH 7.0) to the reaction cell 70 at a flow rate of 0.1 ml/min and maintaining the temperature of the glucose solution at 37° C. The change of the response current with time is shown in FIG. 10. The response current values, which are plotted on the ordinate in FIG. 10, are expressed as relative values when the value at the measurement time "0" is defined as 100.

(2) Response Characteristics of the Enzyme Electrode Before and After Use

Figure 11:
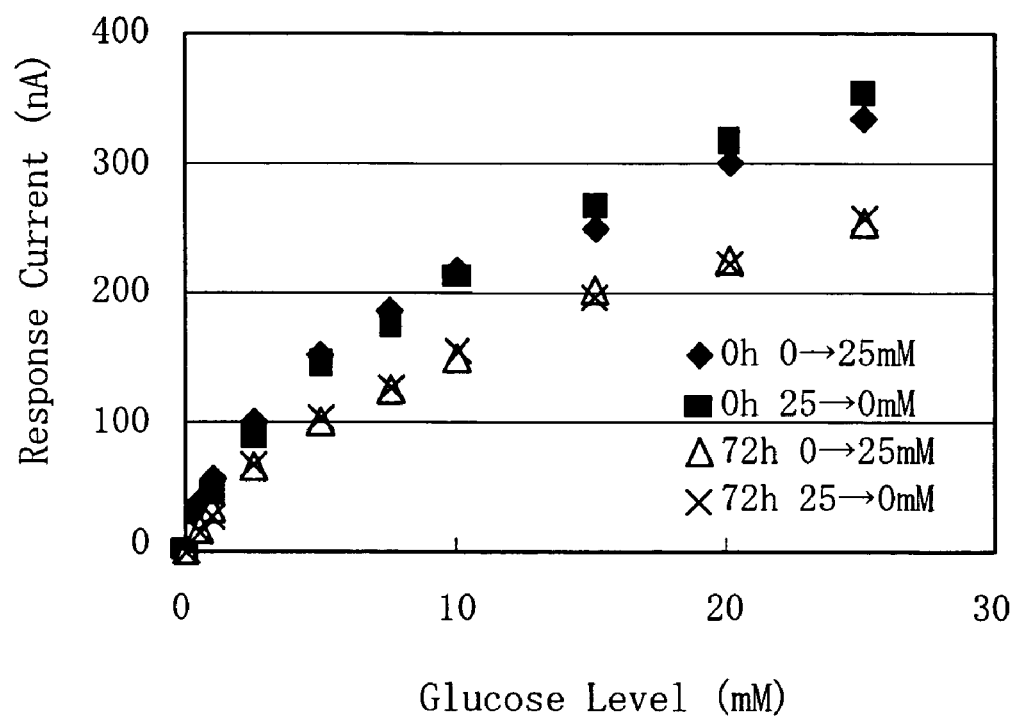
FIG. 11 is a graph showing the measurements of responsive current in the case where the glucose level was changed in Example 3.

The response characteristics of the enzyme electrode before use (0 h) and after use (72 h) were examined based on the response current in applying the voltage of +250 mV, which was measured using the measurement system shown in FIG. 7 while supplying the glucose solution of the intended concentration at a flow rate of 0.5 ml/min and maintaining the temperature of the glucose solution at 37° C. The glucose solution was supplied while increasing the concentration step by step in the order of 0 mM, 0.5 mM, 1.0 mM, 2.5 mM, 10.0 mM, 15.0 mM, 20.0 mM and 25 mM and then reducing the concentration step by step in the reverse order. The measurements of the response current are shown in FIG. 11.

As is clear from FIG. 10, although the response current decreased with time in the 72-hour continuous monitoring test, a certain level of current was measured even after 72 hours. As is clear from FIG. 11, although the enzyme electrode after the use for the 72-hour continuous monitoring is inferior in response characteristics to the enzyme electrode before use, the response characteristics of the used enzyme electrode is sufficient to measure the glucose level. These results indicate that, in the enzyme electrode utilizing GDH in which electron mediator protein is combined, the GDH has sufficient residual activity even after the 72-hour continuous monitoring test and that continuous monitoring is possible by using an enzyme electrode utilizing CyGDH, for example.

Specifically, the continuous monitoring becomes possible by checking the deterioration with time of the response current at the enzyme electrode in advance and correcting the measured value or the computed value based on the estimated deterioration with time. Further, the continuous monitoring becomes possible by improving the enzyme electrode to suppress the deterioration with time. Moreover, the continuous monitoring becomes possible by compensating for the decrement of the responsive current due to the deterioration with time of the enzyme electrode by compulsively increasing the responsive current by increasing the voltage to be applied with time. That is, the continuous monitoring becomes possible by controlling the voltage to be applied in such a manner that the response current as shown in FIG. 11 maintains a constant value.

From the continuous monitoring test, it is found that the decrement of the responsive current is large during about the initial 18 hours, and the responsive current is generally constant thereafter. Therefore, the enzyme electrode (glucose sensor) may be intentionally deteriorated to some degree before the use for the actual glucose level measurement.

As is clear from FIG. 11, in the enzyme electrodes (glucose sensor) before use (0 h) and after use (72 h), a good correlation is found between the process of increasing the glucose level (from 0 mM to 25 mM) and the process of decreasing the glucose level (from 25 mM to 0 mM). This indicates that proper glucose level measurement is possible in the case where the glucose level changes with time, such as when the glucose level is monitored continuously.

The invention claimed is:

1. A glucose sensor comprising a housing, an insulating substrate mounted in the housing, a working electrode formed on the insulating substrate within the housing, a counter electrode formed on the insulating substrate within the housing, a first hollow needle projecting out from the housing that sticks into skin, samples a body fluid, and supplies the body fluid to the working electrode, and a second hollow needle projecting out from the housing that sticks into the skin, samples the body fluid and supplies the body fluid to the counter electrode, the working electrode including a conductive component and glucose dehydrogenase immobilized to the conductive component;

wherein the glucose dehydrogenase is a protein complex including a catalytic activity subunit in which flavin adenine dinucleotide is bound as coenzyme and which has glucose dehydrogenase activity, and an electron mediator subunit for supplying an electron donated from the catalytic activity subunit to the conductive component.

2. The glucose sensor according to claim 1, wherein the glucose dehydrogenase derives from a microorganism belonging to the genus *Burkholderia*.

3. The glucose sensor according to claim 2, wherein the electron mediator subunit is cytocbrome c.

4. The glucose sensor according to claim 3, wherein molecular weight of the catalytic activity subunit in SDS-polyacrylamide gel electrophoresis under reduction conditions is about 60 kDa, whereas molecular weight of the cytochrome c in SDS-polyacrylamide gel electrophoresis under reduction conditions is about 43 kDa.

5. The glucose sensor according to claim 4, wherein the glucose dehydrogenase further includes a γ subunit whose molecular weight in SDS-polyacrylamide gel electrophoresis under reduction conditions is about 14 kDa.

6. The glucose sensor according to claim 1, wherein the glucose sensor is designed to continuously measure a glucose level or successively measure a glucose level a plurality of times while the first and second hollow needles are held in the skin.

7. The glucose sensor according to claim 1, wherein the housing comprises a liquid reservoir for reserving the body fluid sampled through the first and second needles; and
wherein the body fluid reserved in the liquid reservoir is brought into contact with the working electrode and the counter electrode.

8. The glucose sensor according to claim 7, wherein the liquid reservoir comprises a porous body arranged in contact with the working electrode, the counter electrode, the first needle and the second needle.

9. A glucose sensor comprising a housing, an insulating substrate mounted in the housing, a working electrode formed on the insulating substrate, and a counter electrode formed on the insulating substrate, the working electrode including a conductive component and glucose dehydrogenase immobilized to the conductive component;
wherein the glucose dehydrogenase is a protein complex including a catalytic activity subunit in which flavin adenine dinucleotide is bound as coenzyme and which has glucose dehydrogenase activity, and an electron mediator subunit for supplying an electron donated from the catalytic activity subunit to the conductive component; and
wherein the insulating substrate includes a narrowed portion projecting out from the housing for being embedded under skin, at least part of the working electrode and at least a part of the counter electrode being formed on the narrowed portion of the insulating substrate.

10. The glucose sensor according to claim 9, wherein the glucose dehydrogenase derives from a microorganism belonging to the genus *Burkholderia*.

11. The glucose sensor according to claim 9, wherein the glucose sensor is designed to continuously measure a glucose level or successively measure a glucose level a plurality of times while the narrowed portion of the insulating substrate is embedded in the skin.

12. The glucose sensor according to claim 9, wherein the insulating substrate is flexible.

13. The glucose sensor according to claim 10, wherein the electron mediator subunit is cytochrome c.

14. The glucose sensor according to claim 12, wherein the insulating substrate includes a main portion accommodated in the housing, the narrowed portion of the insulating substrate being bent relative to the main portion of the insulating substrate.

15. The glucose sensor according to claim 13, wherein molecular weight of the catalytic activity subunit in SDS-polyacrylamide gel electrophoresis under reduction conditions is about 60 kDa, whereas molecular weight of the cytochrome c in SDS-polyacrylamide gel electrophoresis under reduction conditions is about 43 kDa.

16. The glucose sensor according to claim 15, wherein the glucose dehydrogenase further includes a γ subunit whose molecular weight in SDS-polyacrylamide gel electrophoresis under reduction conditions is about 14 kDa.

17. A glucose level measuring apparatus designed to continuously measure a glucose level or successively measure a glucose level a plurality of times based on a body fluid, the apparatus comprising:
a glucose sensor according to any one of claims 1-6, 7, 8, and 9-16;
a measurer for measuring a response from the glucose sensor;
a computation unit for computing a glucose level based on the measurement by the measurer; and
a controller for controlling timing at which the glucose level is computed at the computation unit.

* * * * *